US009700393B2

United States Patent
Fish et al.

(10) Patent No.: US 9,700,393 B2
(45) Date of Patent: Jul. 11, 2017

(54) DEVICE FOR DELIVERY OF A TOOTH WHITENING AGENT

(71) Applicant: KONINKLIJKE PHILIPS N.V., Eindhoven (NL)

(72) Inventors: David Andrew Fish, Haywards Heath (GB); Nigel David Young, Meadvale (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 219 days.

(21) Appl. No.: 14/359,922

(22) PCT Filed: Dec. 20, 2012

(86) PCT No.: PCT/IB2012/057503
§ 371 (c)(1),
(2) Date: May 22, 2014

(87) PCT Pub. No.: WO2013/093816
PCT Pub. Date: Jun. 27, 2013

(65) Prior Publication Data
US 2015/0017601 A1 Jan. 15, 2015

Related U.S. Application Data

(60) Provisional application No. 61/579,862, filed on Dec. 23, 2011.

(51) Int. Cl.
*A61C 3/02* (2006.01)
*A61C 17/02* (2006.01)
(Continued)

(52) U.S. Cl.
CPC .......... *A61C 17/0202* (2013.01); *A61C 3/025* (2013.01); *A61C 19/063* (2013.01); *A61C 19/066* (2013.01)

(58) Field of Classification Search
CPC . A61C 17/0202; A61C 19/066; A61C 19/063; A61C 3/025; A61M 2202/064; A61M 15/0065
(Continued)

(56) References Cited

U.S. PATENT DOCUMENTS 3,602,398 A * 8/1971 Pollak ................ A61C 17/0214
222/133
4,003,500 A * 1/1977 Schornig .................. G03D 3/02
222/133
(Continued)

FOREIGN PATENT DOCUMENTS

CH WO 2008151457 A1 * 12/2008 ............. A61C 3/025
JP 2007014744 A 1/2007
(Continued)

OTHER PUBLICATIONS

Xuea et al, "Preparation and Characterization of Calcium-Shellac Spheres as a Carrier of Carbamide Peroxide" Microencapsulation, vol. 25, No. 8, 2008, p. 523.
(Continued)

*Primary Examiner* — Matthew Nelson (57) ABSTRACT

A delivery device (12, 140) includes a source (16) of pressurized fluid and a nozzle (24) which defines an outlet (22). A fluid pathway (20) fluidly connects the source of pressurized fluid with the nozzle outlet (22) for delivery of a spray of fluid from the nozzle outlet. A delivery mechanism (14) releases a dose (48) of particles (28) into the fluid pathway from an associated cartridge (32), such that the dose of the particles is carried by the pressurized fluid through the nozzle outlet in the spray. The particles include a dental care agent.

14 Claims, 7 Drawing Sheets

(51) Int. Cl.
*A61C 3/025* (2006.01)
*A61C 19/06* (2006.01)

(58) Field of Classification Search
USPC ................ 433/80, 88, 89, 216; 222/133
See application file for complete search history.

(56) References Cited

U.S. PATENT DOCUMENTS

| | | | | |
|---|---|---|---|---|
| 4,162,868 | A | * | 7/1979 | Stapleton ............... A47G 21/08 119/51.13 |
| 4,184,258 | A | * | 1/1980 | Barrington ............. A61C 3/025 222/636 |
| 4,293,083 | A | * | 10/1981 | Meares, Jr. ............. E03C 1/046 222/133 |
| 5,366,122 | A | * | 11/1994 | Guentert ............... A61M 13/00 128/200.22 |
| 5,568,884 | A | * | 10/1996 | Bruna ............... A61M 15/0065 128/203.13 |
| 6,093,021 | A | | 7/2000 | Rainey |
| 7,591,264 | B2 | * | 9/2009 | Beller ............... A61M 15/0065 128/203.12 |
| 8,181,647 | B2 | | 5/2012 | Ishizeki et al. |
| 8,240,510 | B2 | * | 8/2012 | Kissling ............. B01F 15/0217 222/133 |
| 2006/0081246 | A1 | * | 4/2006 | Goede ............... A61M 15/0065 128/203.15 |
| 2009/0305187 | A1 | | 12/2009 | Janssen et al. |
| 2010/0003520 | A1 | | 1/2010 | Bujard et al. |
| 2010/0065048 | A1 | * | 3/2010 | Mueller-Walz ... A61M 15/0065 128/203.15 |
| 2010/0217671 | A1 | | 8/2010 | Lee et al. |
| 2010/0256554 | A1 | | 10/2010 | Discher, Jr. |
| 2010/0273125 | A1 | * | 10/2010 | Janssen ............... A61C 17/0217 433/80 |
| 2010/0273126 | A1 | | 10/2010 | Janssen et al. |
| 2010/0273127 | A1 | | 10/2010 | Janssen et al. |
| 2011/0207078 | A1 | | 8/2011 | Johnson et al. |
| 2011/0244418 | A1 | | 10/2011 | Edwards et al. |
| 2012/0312844 | A1 | * | 12/2012 | Chatterjee ............... G01F 11/18 222/636 |

FOREIGN PATENT DOCUMENTS

| | | |
|---|---|---|
| WO | 0213721 A1 | 2/2002 |
| WO | 2004112637 A2 | 12/2004 |
| WO | 2005113042 A1 | 12/2005 |
| WO | 2008151457 A1 | 12/2008 |
| WO | 2010055435 A1 | 5/2010 |

OTHER PUBLICATIONS

Xue et al, "Physical, Structural and Mechanical Characterisation of Calcium-Shellac Microspheres as a Carrier of Carbamide Peroxide", J. Applied Polymer Science, vol. 113, 2009, p. 1619.

* cited by examiner

DEVICE FOR DELIVERY OF A TOOTH WHITENING AGENT

CROSS-REFERENCE TO PRIOR APPLICATIONS

This application is the U.S. National Phase application under 35 U.S.C. §371 of International Application No. PCT/IB2012/057503, filed on Dec. 20, 2012, which claims the benefit of U.S. Provisional Application No. 61/579,862, filed on Dec. 23, 2011. These applications are hereby incorporated by reference herein.

The following relates to the dental cleaning arts, and related arts and more specifically concerns a mechanism and a device for delivering an active agent for dental care, such as a tooth whitening agent for whitening teeth.

Tooth whitening agents are generally hydrogen peroxide-based and the aim is generally to deliver the peroxide to the teeth in a sufficient amount to effect a color change in the surface of the teeth in an acceptable period of time without causing harm to the user. Various methods have been developed for applying tooth whitening agents to the teeth. These include toothpastes, peroxide gel strips, whitening solutions, and mouthwashes. Abrasive toothpastes, while easy to use, are generally ineffective. Peroxide gel strips are somewhat more effective, but entail wearing a plastic strip on the teeth to be treated for an extended period. Mouthwashes, which are solutions of peroxide, can be harmful due to contact of the solution with soft tissues. Dental trays use a high concentration of peroxide solution. As a result, great care is needed to avoid contact of the peroxide with soft tissue. Such methods are therefore best suited to use in a dental surgery.

Another problem with hydrogen peroxide is that it rapidly decomposes and becomes ineffective as a bleaching agent. Recently, methods have been developed for encapsulating carbamide peroxide, a dry source of hydrogen peroxide, which is an adduct of urea and hydrogen peroxide. See, Jing Xue and Zhibing Zhang, "Preparation and characterization of calcium-shellac spheres as a carrier of carbamide peroxide," J. Microencapsulation, 25(8), p. 523 (2008); and Jing Xue and Zhibing Zhang, "Physical, Structural and Mechanical Characterisation of Calcium-Shellac Microspheres as a Carrier of Carbamide Peroxide," J. Applied Polymer Science, Vol. 113, p. 1619 (2009).

Such spheres are suggested for being combined in a carrier material, such as a toothpaste or gum. However, moisture in the carrier material may cause the hydrogen peroxide to be released and decompose before the material is used for teeth whitening. Another disadvantage of this method is that the particles cannot be directed to where they are needed, resulting in particle wastage and contact with soft tissue which is undesirable.

A device for delivery of a tooth whitening agent and a cartridge containing encapsulated whitening agent for use therewith are disclosed which can overcome some of the problems with existing delivery systems.

In accordance with one aspect of the invention, a delivery device includes a source of pressurized fluid, a nozzle which defines an outlet, and a fluid pathway which fluidly connects the source of pressurized fluid with the nozzle outlet for delivery of a spray of fluid from the nozzle outlet. A delivery mechanism releases a dose of particles into the fluid pathway from an associated cartridge, such that the dose of the particles is carried by the pressurized fluid through the nozzle outlet in the spray, the particles comprising a dental care agent.

In accordance with another aspect, a method for delivery of particles includes providing a cartridge of particles in a delivery device, the particles comprising a dental care agent. A delivery mechanism is actuated to deliver a dose of the particles from the cartridge to a fluid pathway and cause a flow of pressurized fluid to flow from a source of the pressurized fluid to the dose of particles in the fluid pathway and transport the particles to a nozzle outlet of the delivery device, whereby the particles are ejected from the device in a spray of the pressurized fluid.

In another aspect, a delivery mechanism includes a housing which defines a channel, a fluid pathway, and a slider carried by the housing. The slider is moveable, within the channel, between a first position, in which the slider accepts a dose of particles from an associated cartridge, and a second position, in which the dose of particles is released into the fluid pathway. The housing defines first and second openings to the channel which are closed by the slider when the slider is in the first position, and which are open to the channel when the slider is in the seconds position, wherein in the second position of the slider, the openings define a part of the fluid pathway and the dose of particles is positioned in the second opening.

An advantage of the exemplary delivery device is that particles containing a bleaching agent are maintained in a dry state until needed. Another advantage of the exemplary delivery device is that the particles are directed at the teeth.

The invention may take form in various components and arrangements of components, and in various process operations and arrangements of process operations. The drawings are only for the purpose of illustrating preferred embodiments and are not to be construed as limiting the invention.

As used herein the terms "upper" and "lower," and the like, are made with reference to the position of the device or part thereof as shown in the referenced drawing and it is to be appreciated that in use the device may assume different positions.

Figure 1:
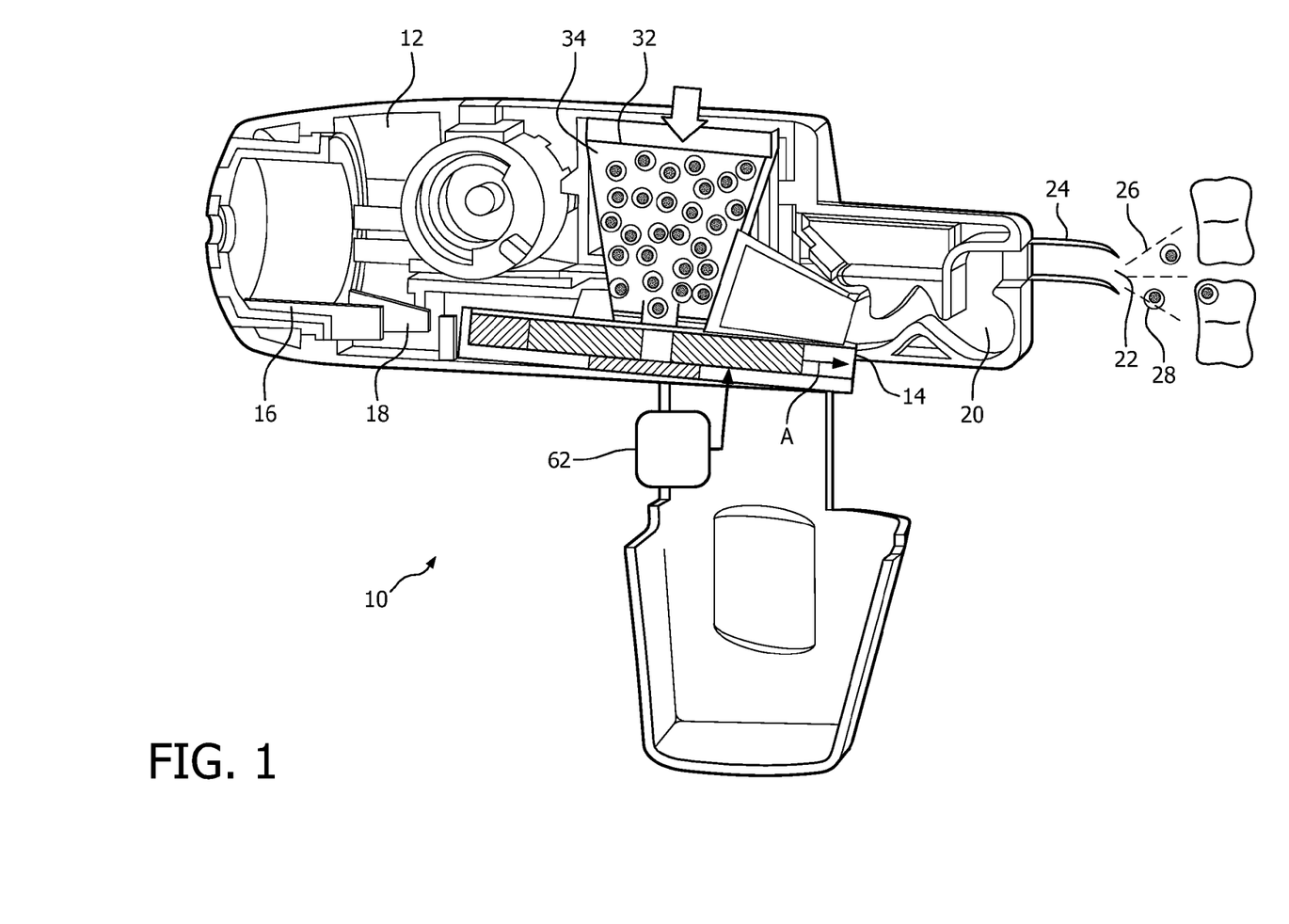
FIG. 1 diagrammatically shows a perspective view, in partial cross section, of a first embodiment of a delivery device which incorporates a delivery mechanism for delivery of particles from a capsule.

With reference to FIG. 1, a schematic cross sectional view of a delivery system 10 is shown. The delivery system 10 includes a delivery device 12 which includes a particle delivery mechanism 14. The device 12 includes a source 16 of a pressurized delivery fluid, which may be carried by a body portion 18 of the device 12. A pathway 20 fluidly connects the source 16 of pressurized fluid with an outlet 22 of a nozzle 24. While the exemplary source 16 includes a fan for delivery of pressurized air, in other embodiments, a pressurized container of gas or a spring loaded piston system may be used as the fluid source. Typically, the nozzle outlet will be 0.5-2 mm in diameter. This enables delivery of a spray 26 of the pressurized fluid, together with particles 28 (not to scale) from the nozzle outlet 22. The particle-containing spray 26 is applied to the teeth 30 of a person or other dentate animal. A cartridge 32 of particles is received in the delivery device 12. The cartridge defines a reservoir 34 which contains a large number of the particles 28 to be dispensed in small doses into the pathway 20. In operation, a dose of particles 28 (e.g., microparticles) is carried from the cartridge 32 by the pressurized delivery fluid and through the nozzle outlet 22. The cartridge can be made from a plastic material, such as a polycarbonate, although other materials can be used.

The exemplary particles 28 include a dental care agent. The dental care agent can include a tooth whitening agent, such as a bleaching agent, and/or other dental care agents, such as fluoride (e.g., NaF), antibiotics, remineralization agents, or pain relief agents ($KNO_3$), combinations thereof and the like. While particular reference is made herein to tooth whitening using peroxide-based dental care agents, it is to be appreciated that other applications and/or dental care agents are also contemplated.

Figure 2:
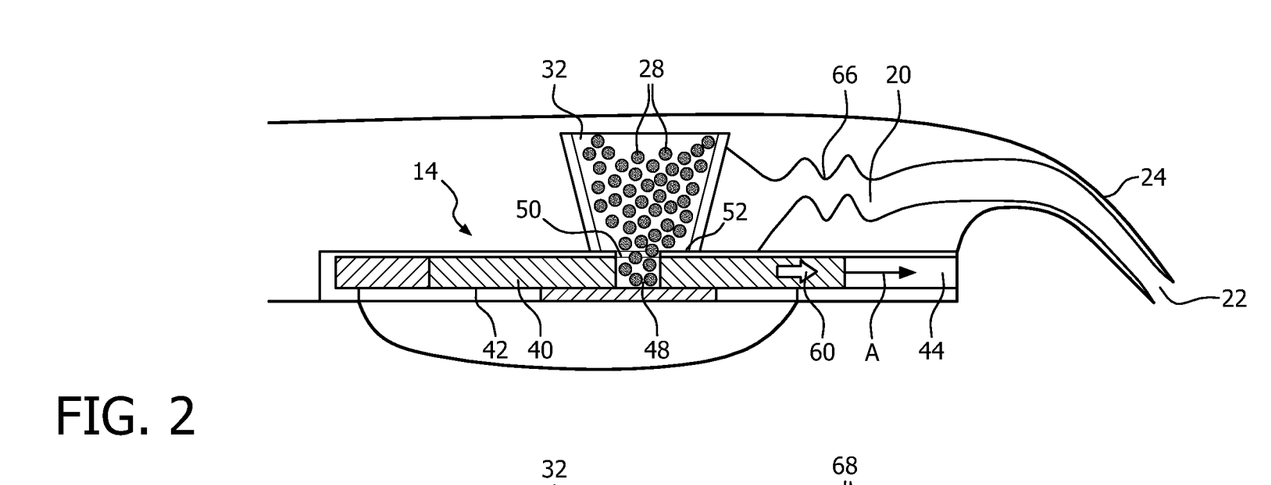
FIG. 2 diagrammatically shows a cross sectional view of a first embodiment of the delivery mechanism for delivery of a tooth whitening agent in a first position.
Figure 3:
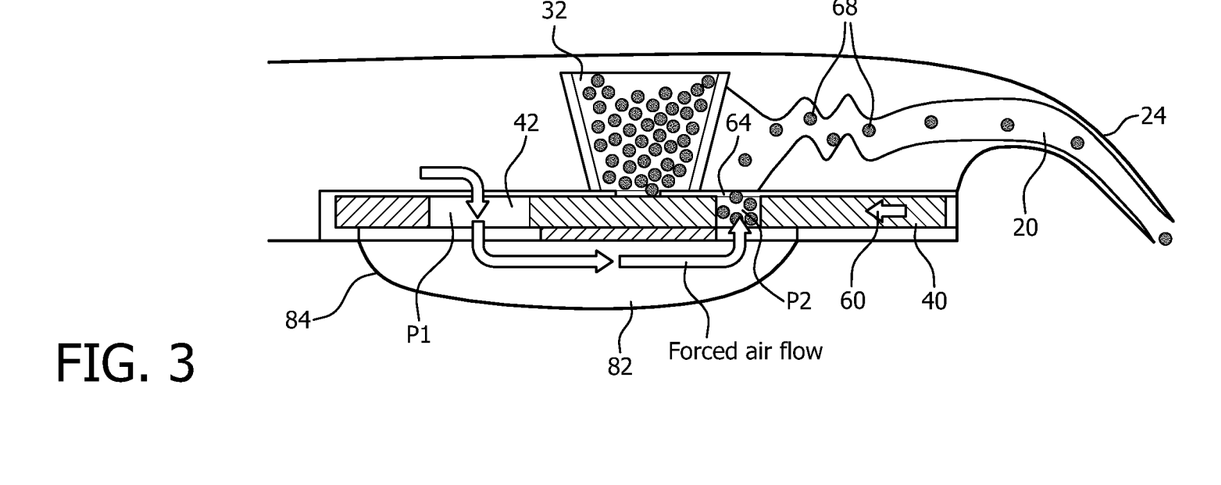
FIG. 3 diagrammatically shows a cross sectional view of the delivery mechanism of FIG. 2 in a second position.

As illustrated in FIGS. 2 and 3, the particle delivery mechanism 14 is configured for supplying particles 28 from the cartridge into the pathway 20 in controlled amounts. The exemplary delivery mechanism includes a slider 40 which is carried by a housing 42. The slider 40 is traversed, along a channel 44 within the housing, in the direction of arrow A from a first position, shown in FIG. 2, to a second position, shown in FIG. 3. The slider cooperates with the housing to define an upwardly open cavity 46, which is sized to receive a small dose 48 of the particles 28 from the cartridge 32 when the slider is in the first position. In general, each dose 48 is only a small proportion of the particles contained in the cartridge, such as 10% of the particles, or less, at least initially. The cartridge 32 defines a suitably positioned opening 50 in an end wall 52, which is sized to allow particles to drop into the cavity 46, or to be forced into the cavity under pressure. In particular, the cavity 46 includes an open, first end 54, adjacent the cartridge, and a second opposed end 56, which is closed, in this first position of the slider, by the housing 42. In this position of the slider 40, access to the pathway 20 is closed by the slider 40, so the particles in the reservoir 34 and cavity 46 do not come into contact with pressurized fluid, which may contain water droplets in one embodiment.

As illustrated in FIG. 3, the housing 42 and the slider 40 cooperate, in this position, to define a portion of the pathway 20 whereby pressurized fluid flows through the housing and carries the particles out of the cavity into the nozzle 24.

An actuator mechanism 60 for the slider 40 may include a drive motor, or the like, which drives the slider in the direction of arrow A. Mechanism 60 is illustrated figuratively by an arrow in FIG. 2. A button 62 (FIG. 1) may be provided on the device for activating the actuator mechanism 60 and optionally also the source of fluid.

As illustrated in FIG. 3, the housing 42 and the slider 40 cooperate, in this second slider position, to define a portion of the pathway 20 whereby pressurized fluid flows through the housing and carries the particles out of the cavity into the nozzle 24.

An actuator mechanism 60 for the slider 40 may include a drive motor, or the like, which drives the slider in the direction of arrow A. Mechanism 60 is illustrated figuratively by an arrow in FIG. 2. A button 62 (FIG. 1) may be provided on the device for activating the actuator mechanism 60 and optionally also the source of fluid.

Upon activation of the device 10, e.g., by pressing button 62, air or other pressurized fluid is forced through the mechanism 14 and at the same time the slider is moved laterally to take the dose of particles from the cavity under the reservoir 34 to an ejection point 64 where the air flow takes the particles into the exit nozzle 24. In one embodiment, a baffle 66 is positioned in the exit nozzle 24. The exemplary baffle is defined by bends in the pathway which created surfaces 68 which are angled to the fluid flow. These angled surfaces 68 cause the particles to impact upon a hard surface and this causes them to rupture so that when they adhere to the tooth, they can disperse their dental care agent (e.g. hydrogen peroxide) load in a reasonable time. As will be appreciated, other types of baffles, such as walls extending into a generally straight passage which are configured to intercept the fluid flow are also contemplated. After actuation and release of the particles the slider moves back to its position with the cavity under the reservoir and is refilled with a new dose of particles. In this way, the particles in the reservoir remain dry and do not come into contact with the fluid. The dry storage avoids degradation of the peroxide or other dental care agent in the particles over time.

Figure 4:
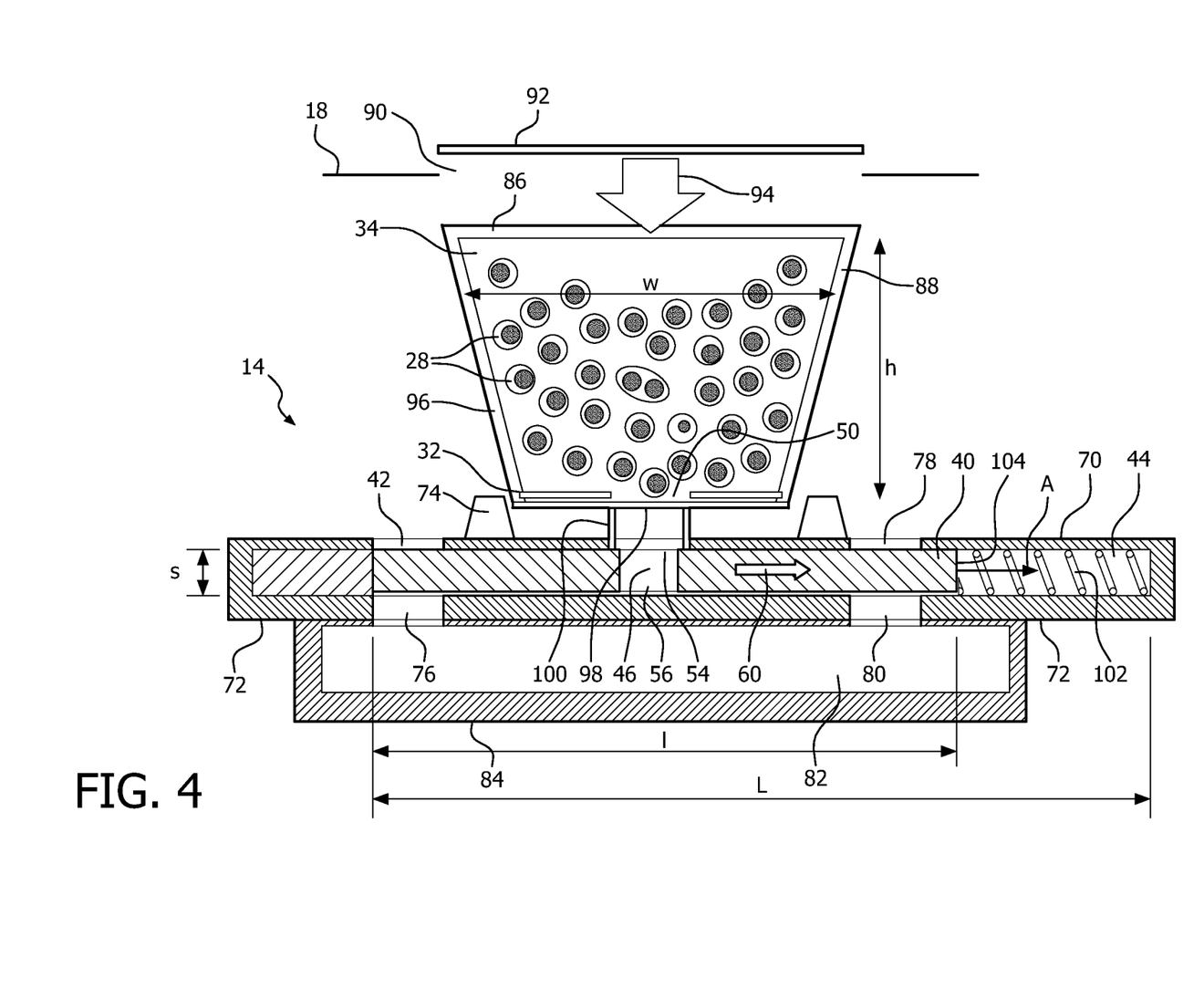
FIG. 4 diagrammatically shows a cross sectional view of a second embodiment of a delivery mechanism for delivery of a tooth whitening agent in a first position.

Turning to FIG. 4, which shows an enlarged view of the mechanism 14 and cartridge 32, the slider has a length/ between its first and second ends. The slider 40 has a generally uniform cross section of height s, over most of its length l. The length l is generally greater than the cross sectional height s and width. The cross section corresponds, in dimension, to the cross section of the channel 44. The cross section of the slider is only slightly smaller than that of the channel, to allow the slider to move within it, while engaging the channel walls snugly. In one embodiment, the cross section is rectangular, although in other embodiments another polygonal shape or a circular cross section is also contemplated. The channel has a length L which is greater than the length l of the slider.

In the illustrated embodiment, the housing 42 includes upper and lower parallel, planar walls 70, 72, which define the height h of the channel 44 therebetween. As will be appreciated, the housing 42 also defines end walls at ends of the channel, and side walls (not shown), which connect the planar walls 70, 72 and which define the width of the channel therebetween. In use, the upper wall 70 of the housing engages the cartridge 32 and/or is fixed in position, relative to the cartridge. A first pair of opposed openings 74, 76 is defined in the upper and lower walls 70, 72, respectively, upstream of the reservoir 34, and a second pair of opposed openings 78, 80 is defined in the upper and lower walls 70, 72, downstream of the reservoir. The openings 76, 80 are connected by a portion 82 of the pathway 20, which may be defined by a sealed enclosure 84 connected with the lower wall 72 of the housing. In the slider first position, the openings 74, 76 and 76, 80 (or at least one of each pair) are closed to the pathway 20/pathway portion 82 by the slider 40. In this position, the cavity 46 is located intermediate the first pair and the second pair of openings. As the slider 40 begins to move into the position shown in FIG. 3, a first fluid passageway P1 is created between the openings 74, 76. Specifically, these openings are now aligned with a gap 85 which has been created between the slider first end and an end wall of the housing. The pressurized fluid can enter the enclosure 84 through the passageway creating a pressurized pathway potion 82. At this time, the second pair of openings is still closed by the slider. When the slider reaches the position in FIG. 3, a second passageway P2 is created through the openings 78, 80. Specifically, these openings are now aligned with cavity openings 54, 56. P2 is thus created slightly after the creation of the first passageway P1. The pressure from within the enclosure 82 acting on the opening 80 forces the particles 28 out of the opening 78. After releasing the dose of particles, the slider is returned to the first position, and the process can be repeated.

The slider 40 and housing 42 can be formed form any suitably rigid material, such as metal or plastic. The slider can be substantially solid, with the cavity 46 defined by a bore through the slider.

With continued reference to FIG. 4, the exemplary cartridge 34 includes upper and lower end walls 86, 50 that are connected with and spaced by cylindrical side wall 88. The illustrated cartridge is frustoconical in shape, although cylindrical or other regular polygons are also contemplated. In one embodiment the end wall 86 is flexible, allowing it to assume a concave shape under an external pressure, thereby putting pressure on the particles in the reservoir and forcing them towards the opening 50.

The cartridge 32 may be from 0.01-2 cm in height h and/or width (average diameter) w, such as from 0.05-0.5 cm in height and/or width.

The cartridge 32 can be a removable cartridge which is fitted into the body 18 of the device through a suitably positioned opening 90 in the body. The opening 90 may be thereafter closed by a closure member 92, such as a door, which holds the cartridge in position on the mechanism. For example, a biasing member 94, such as a spring, is connected with an inner surface of the closure member to press the cartridge 32 into engagement with the upper wall of the housing. A guide member 96, such as an annulus, guides the cartridge into the correct position during closing of the door, and may grip the cartridge. The guide member may be mounted to the housing wall 70 and serve as a receptacle for the cartridge.

As shown in FIG. 4, the cartridge 32 may be sealed against ingress of moisture, during storage with a seal 98. The seal 98 covers the opening 50 in the cartridge. The seal may be a frangible membrane formed from plastic and/or metal foil, for example, which can be broken to expose the cartridge opening. In one embodiment, the device includes a cutting member, such as a sharp edged ring, which automatically breaks the membrane as the cartridge is inserted in the device. In another embodiment, the cartridge may be fitted with a pull-off or breakable seal or the like which the user removes/breaks just prior to use.

Figure 5:
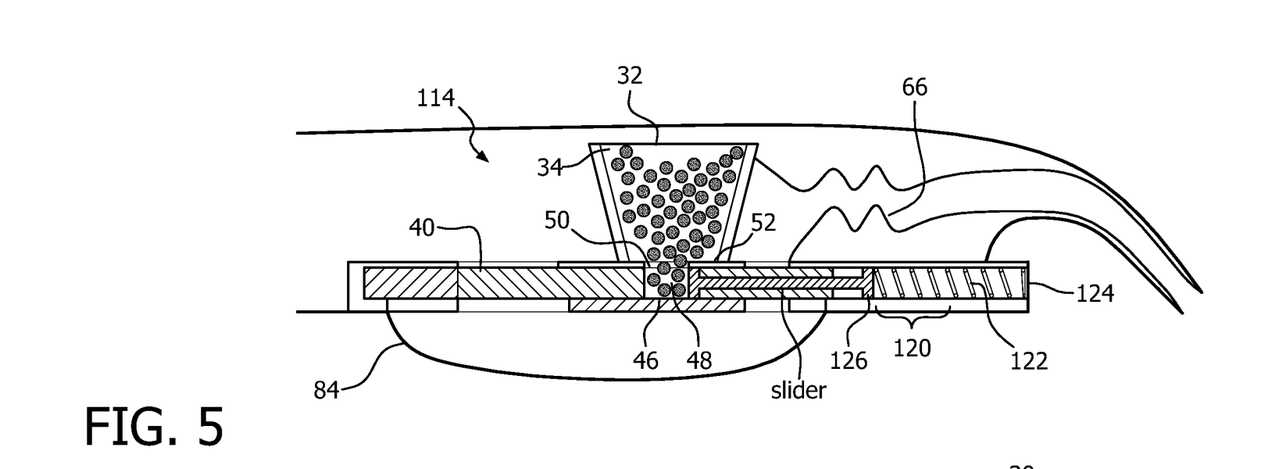
FIG. 5 diagrammatically shows a cross sectional view of the delivery mechanism of FIG. 4 in a second position.

The slider actuator mechanism 60 may actuate the slider to move in one or both directions. In other embodiments, the slider may be biased to one of the first and second positions by a biasing mechanism 102, such as a spring. For example, as shown in FIG. 5, a spring is positioned in the channel 44 between the slider and an end wall of the housing and contacts the slider at an end 104 nearest the exit point 78. The spring may automatically return the slider to the first position when the actuator mechanism 60 disengages.

Figure 6:
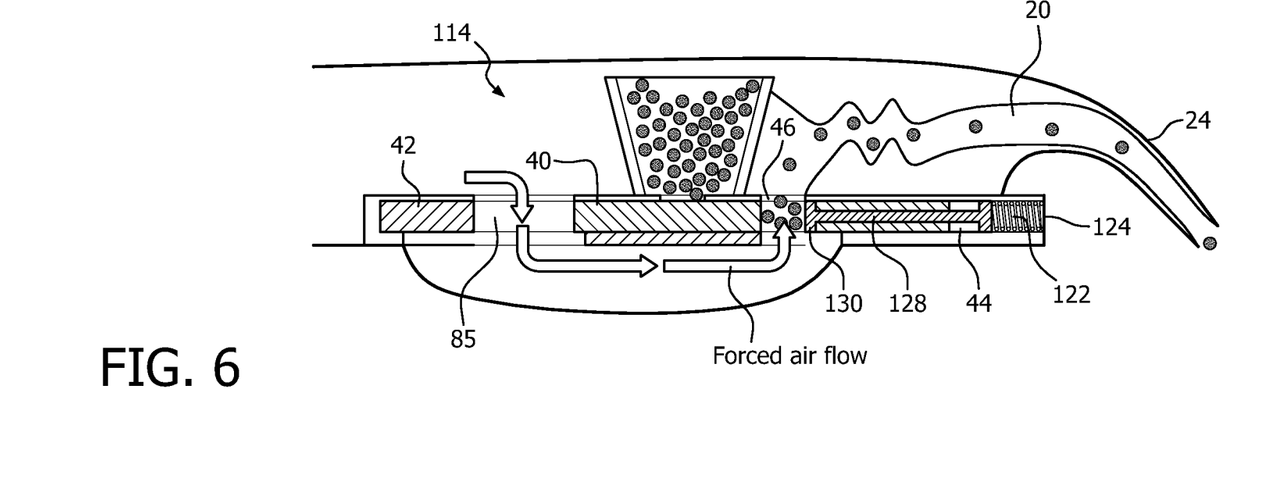
FIG. 6 diagrammatically shows a perspective view, in partial cross section, of a second embodiment of a delivery device which incorporates the delivery mechanism of FIGS. 2 and 3.

FIGS. 5 and 6 show another embodiment of the particle delivery mechanism 114, where similar elements are accorded the same numerals and new elements are accorded new numerals. As for the mechanism 14 of FIGS. 2-4, the mechanism 114 is configured for supplying particles 28 from the cartridge into the pathway 20 in controlled amounts. The exemplary delivery mechanism includes a slider 40 which is carried by a housing 42. The slider 40 is traversed, along a channel 44 within the housing, in the direction of arrow A from a first position, shown in FIG. 5, to a second position, shown in FIG. 6. The slider cooperates with the housing to define an upwardly open cavity 46 sized to receive a small dose 48 of the particles 28 from the cartridge 32 when the slider is in the first position. The cartridge defines a suitably positioned opening 50 in an end wall 52, which is sized to allow particles to drop into the cavity 46, or to be forced into the cavity under pressure. In this position of the slider 40, access to the pathway 20 is closed by the slider 40, so the particles in the reservoir 34 and cavity 46 do not come into contact with pressurized fluid, which may contain water droplets in one embodiment.

In this embodiment, the delivery mechanism 14 includes a compression mechanism 120 which compresses the particles 28 in the cavity 46, causing them to rupture. The exemplary compression mechanism includes a spring 122 which is mounted, at a first end, to an end wall 124 of the channel. A plunger 126 is carried by the other end of the spring. A shaft 128 of the plunger 126 is axially mounted through the slider 40 so as to extend into the cavity 46 where it terminates in a flange 130. As the slider 40 is moved to the particle release position, the weak spring 122 is compressed and this enables a small force to be applied to the particles in the dose release section of the device. Upon reaching the release point, all the particles (or at least a proportion of them) are ruptured and released into the exit nozzle. The baffle 66 may still be employed in this embodiment, as the action of forcing particles 28 together to rupture them may also cause them to adhere to one another. Therefore, the baffle can serve to separate the particles again.

In use, a user may actuate the slider and pressured fluid several times during a whitening procedure to deliver several bursts of particles to the teeth. On impact with the teeth, particles which have not already ruptured may rupture to release the bleaching agent within them. In other embodiments, the particles may include a release agent which progressively releases the bleaching agent, as described in further detail below.

The exemplary delivery device 12 can be driven by water or air or both. The delivery fluid can thus be a gas, a liquid, or combination thereof. An exemplary delivery fluid is an atomized liquid in a gas. The liquid can be water or an aqueous solution. The gas can be air, oxygen, carbon dioxide, nitrogen, or the like. In other embodiment the device provides an aerosol of particles in gas only, without liquid.

Various dental devices exist for delivery of fluids to the oral cavity which may be adapted to use for delivery of the capsules 28. As examples, delivery devices are disclosed in U.S. Pub. Nos. 2009/0305187; 2010/003520; 2010/0273125; 2010/0273126; 2010/0273127; 2010/0217671; 2011/0207078; 2011/0244418; and WO 2010/055435. Such devices have been particularly useful for cleaning of interproximal spaces. The devices often generate liquid droplets by merging liquid flowing from a reservoir into a fast-moving gas stream, such as provided by a source of compressed gas. The devices are activated by a user operating a button or the like, releasing successive bursts of compressed gas, which results in a high velocity gas stream. When this high velocity gas stream comes into contact with a flow of liquid from the reservoir, liquid droplets are produced.

Figure 7:
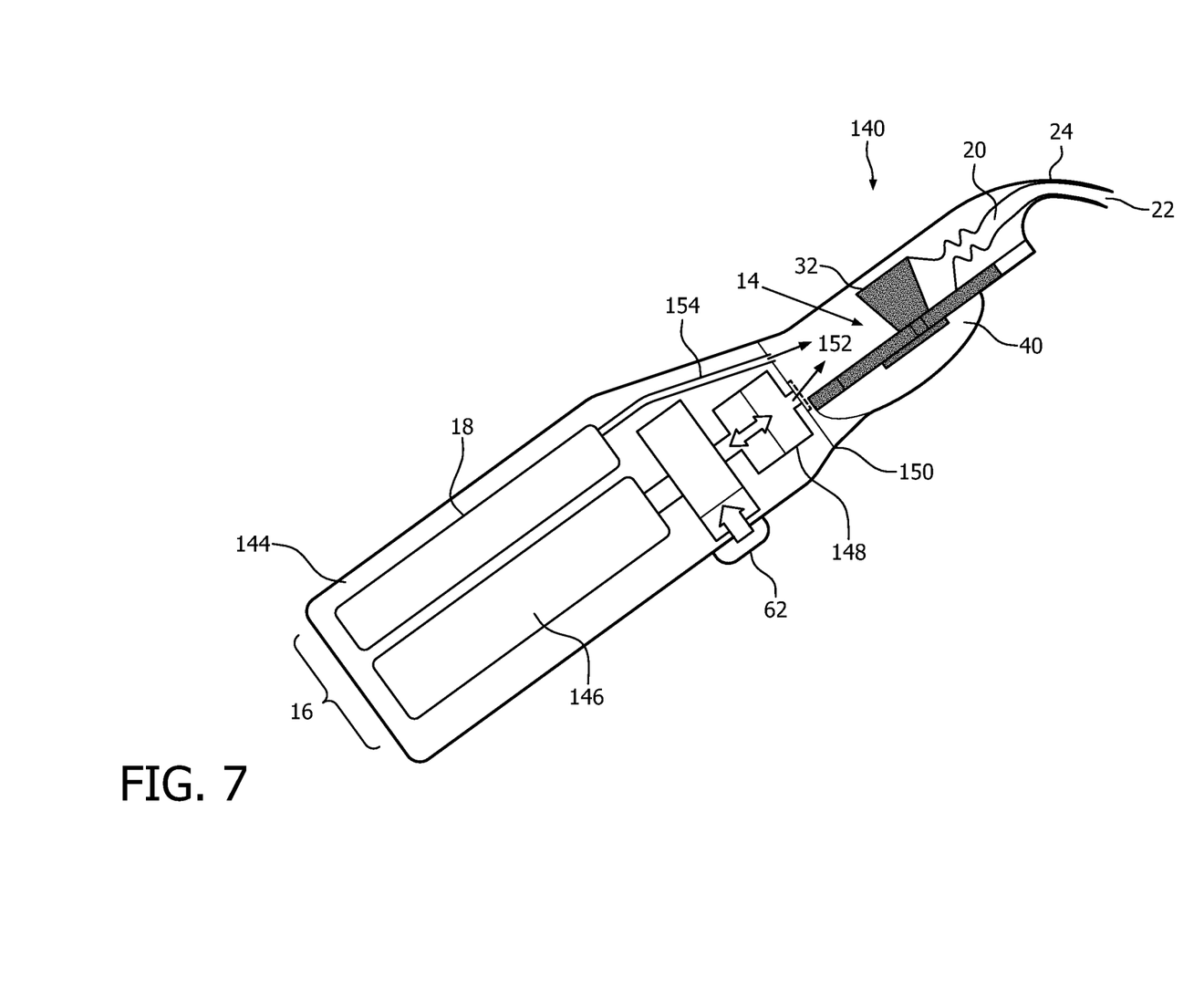
FIG. 7 illustrates an exemplary capsule during insertion in the delivery device of FIG. 1.

FIG. 7 illustrates another embodiment 140 of a device for delivery of bleaching agent particles to the teeth in which such a device is adapted for whitening. The device can be similar, in many respects, to that of FIG. 1, where, similar elements are accorded the same numerals and new elements are accorded new numerals. In this embodiment, the delivery mechanism 14, 114 may form a part of a removable nozzle assembly 142 which may be interchangeable with a conventional nozzle assembly used for cleaning without particles. As for the device 12 of FIG. 1, the device 140 includes an actuation mechanism 62, for causing the device to deliver the high pressure fluid from the fluid source 16. Any suitable actuation mechanism may be employed, such as a switch, button, or the like which directly or indirectly (e.g., via an electrical circuit, pump, a syringe with a gear operated plunger, gas cylinder release valve, or the like) causes high pressure fluid (e.g., gas) to be released by the source 16. For example, the device 140 provides pulses of gas and/or liquid at high velocity, each pulse producing sufficient force to dislodge particles from the cavity 46 and then direct them to the tooth in a manner similar to which an inter-dental cleaning device directs water droplets to the tooth surface. The device shown in FIG. 7 uses atomized water in pulses of air, although air jets alone could also be used to dislodge and transport the particles to the tooth surface. By activating the device repeatedly, e.g., via depressing the button 62, the device produces many pulses of air/water and accompanying doses of particles from the delivery mechanism 14 or 114.

The source 16 of delivery fluid may include a reservoir 144, which holds a supply of water, and a gas source 146. The water from the reservoir may be delivered to the pathway by a pump, by aspiration, or other suitable mechanism. The gas source 146 may include a canister containing a pressurized gas or a mechanism for pressurizing air at atmospheric pressure. Suitable pressurizing mechanisms are disclosed, for example, in U.S. Pub. No. 2011/0244418. As an example, the pressurizing mechanism may include a syringe with a barrel containing air. A plunger, movable within the barrel, is automatically actuated by an associated gear mechanism to reduce the volume inside the syringe barrel and thereby pressurize the air before it is released into the pathway 20. Alternatively, the air may be pressurized by a pump 148. A tube 150 carries the air to a mixing zone 152. A separate tube 154 carries water from the water reservoir 144 to the mixing zone, where it atomizes (forms small droplets) in the air. The illustrated mixing zone 152 is in the pathway 20 upstream of the delivery mechanism 14, such that a mixture of air and water forces the particles from the cavity 36. In other embodiments it is contemplated that the water may mix with the air and particles at a mixing zone downstream of the delivery mechanism, e.g., in the nozzle 24.

The pressure of the fluid exiting the nozzle outlet 22 in the embodiments disclosed herein can be, for example, from 0-20 N/cm$^2$ (0-2 Bar), e.g., at least 1 N/cm$^2$. The gas source 146 may deliver air at a velocity of up to 600 meters per second (m/s), e.g., a velocity of at least 10 or at least 30 m/s, and in some embodiments, up to 200 or 300 m/s. The velocity and size of the water droplets can also vary. For example, the droplets may have a size in the range of 5-500 micrometers, and velocity of, for example, in a range of 10-300 meters m/s.

The device disclosed in WO 2010/055435, for example, can eject water droplets at velocities from 10 to 100 m/s, which is sufficient for delivery of the particles 28 disclosed herein, although higher or lower velocities may be appropriate in some embodiments. The force exerted on the particles 28 when impacting a hard surface, such as a tooth, can be estimated based on the average particle size and density. Assuming, for example, a particle size of 20 μm diameter and a density of 1 g/mL, each particle has a mass of approximately 30 nanograms. Taking a velocity of about 50 m/s and a deceleration distance of 10 μm, the force exerted on the particle on impact will be about 7.5 mN. This is generally sufficient to cause the particles to adhere well to the teeth, and in some embodiments, for the particles to rupture.

In some embodiments, the nozzle and/or the fluid source 16 is configured for providing a higher fluid pressure when the device 12, 140 is used for whitening than when it is used without the whitening particles. In one embodiment, the delivery device 12, 140 has a first nozzle assembly configured for delivery of fluid without the capsules and a second nozzle assembly, interchangeable with the first nozzle assembly, which is specifically adapted to the delivery of the capsules. For example, nozzle assembly 142 includes an engagement member, such as a threaded cap, which is engageable with a mating engagement member, such as a threaded neck of the body 18.

In some embodiments, the device may be configured to provide a first gas flow suited to use of the device 12, 140 in a mode without the particles 28 and a second gas flow, higher than the first, suited to use of the device 12 in a mode when the whitening particles are being used. In some embodiments, the change in pressure is achieved through different nozzle designs for the two modes or through the trigger mechanism.

Figure 8:
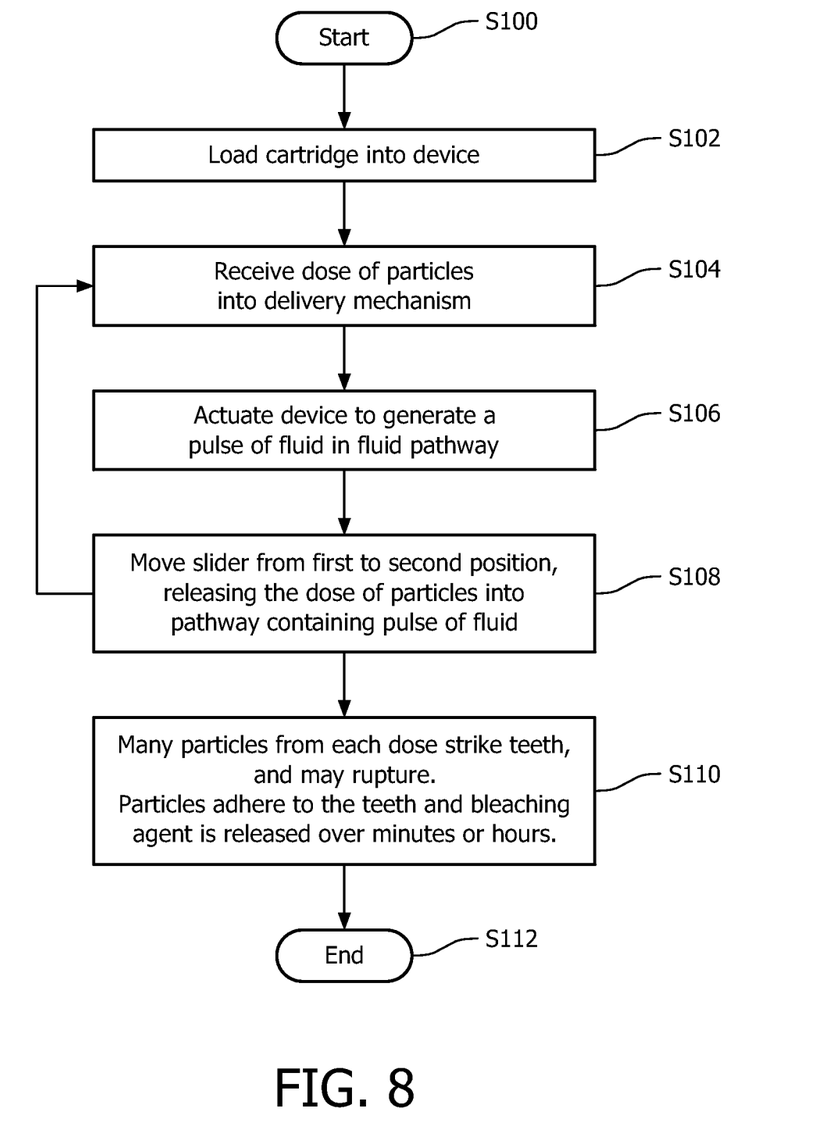
FIG. 8 illustrates a method of delivering particles in accordance with another aspect of the exemplary embodiment.

FIG. 8 summarizes the exemplary method for delivering the particles 28 to a hard surface, such as the teeth. The method begins at S100. At S102, a cartridge is loaded into the device 12, 140. The cartridge 32 of particles is inserted into the device through the opening 90 in the body so that the opening 50 to the reservoir is positioned over the cavity 46, in the first position of the slider 40, using the guide member 96 to guide the insertion. In other embodiments, the cartridge of particles is disposable along with the nozzle, and so need not be inserted into the device. The membrane 98 may be broken during the closing of the door 92.

With the slider in the first position, a dose 48 of particles is received by the delivery mechanism 14 (S104). The device is actuated at S106. For example, the user actuates the device by pressing the button/trigger 62. This generates a pulse of fluid. In particular the device causes a jet of the pressurized fluid to flow through the pathway 20 towards the pressurization chamber 82. (This releases the particles into the fluid flow when the flow path is subsequently completed through the openings 78, 80.)

At S108, the slider is moved toward the second position and the pressurization chamber 82 is pressurized by the pulse of fluid. As the slider reaches its second position, adjacent the second ends of the channel, the particles are released into the fluid pathway. As will be appreciated, S106 and S108 can take place contemporaneously. At S110, particles are ejected from the nozzle strike the teeth and may rupture. The method may return from S108 to S104 for one or a plurality of repeats of S104-S108. Over a period of minutes or hours, the whitening agent is released and effects a whitening of the teeth. The method ends at S112. The cartridge may be left in the device until it is empty.

The particles adhere to the teeth and may rupture. The whiteness of the particles or other color, can be used as an indicator to enable the user to see where the particles have already been applied. The cartridge can remain in the device for a subsequent bleaching operation at a later time, such as one or more days later, since the remaining particles remain dry in the reservoir.

Particles 28 of small size adhered to the tooth can be significantly unnoticeable by touch or sight (their color can be white), so are not a nuisance to the wearer. The user may apply the particles before going to bed so that the dental care agent (e.g., peroxide) action on the teeth occurs overnight. Tooth brushing in the morning can remove any particulate remnants. The user may repeat the process, as needed. The device 12, 140 acts to concentrate the particles on the tooth by repeated jets of particles projected onto the front teeth area. This provides a targeted method of peroxide application. Particles that miss the teeth will generally be at low concentrations elsewhere in the mouth. Additionally, as they will likely not have struck a hard surface, they will tend to release peroxide at a rather slow rate. Since the total concentration of peroxide in the particles of each dose 48 (or even in a set of doses, for example, 2-20 such doses), is controlled and quite small, the method can be considered safe for home use.

In one embodiment, the velocity of the particles 28 is sufficient to cause them to rupture upon hitting the tooth. In this embodiment, the particles may be of a form that enables them to rupture upon impact. In another embodiment, the particles 28 have an outer layer which becomes permeable, e.g., thorough dissolution of the layer or components hereof, water absorption by the layer, or the like. The exemplary particles may have a density which is less than that of water, for example, less than 0.9 g/cm$^3$ at 25° C.

The exemplary particles 28 can be dry, solid particles of at least 1μm in diameter on average, and up to about 200μ in diameter, e.g., 10-100 μm in diameter, on average, and in one embodiment, 20-50 μm on average. Each particle 28 includes a dental bleaching agent (whitening agent) protected by a moisture-resistant material. The bleaching agent may form a core of the particle, which is encapsulated in the moisture-resistant material which forms an outer layer of the particle that surrounds and protects the core from exposure to moisture during storage.

Exemplary bleaching agents are solid at ambient conditions and include carbamide peroxide, which is an adduct of urea and hydrogen peroxide ($CH_4N_2O$—$H_2O_2$). The material releases hydrogen peroxide on contact with water. Other example bleaching agent sources include alkali metal percarbonates, sodium perborate, potassium persulfate, calcium peroxide, zinc peroxide, magnesium peroxide, strontium peroxide, other hydrogen peroxide complexes, sodium chlorite, combinations thereof, and the like. The particles 28 can include bleaching agent, e.g., carbamide peroxide, at a concentration of at least 10 wt. %, such as up to about 40 wt. %. For example, at about 20 wt. %. carbamide peroxide, the hydrogen peroxide concentration per particle 28 is about 6%, which is comparable to whitening strips.

Figure 9:
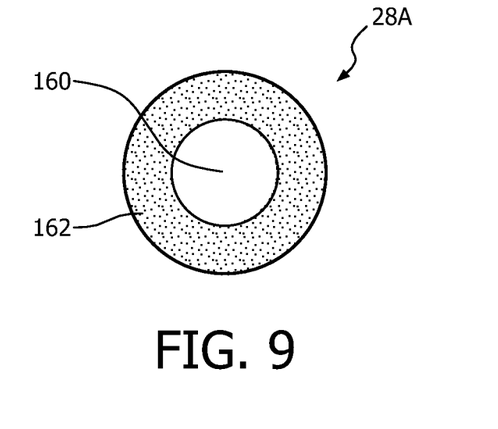
FIGS. 9-11 illustrate exemplary particles.
Figure 10:
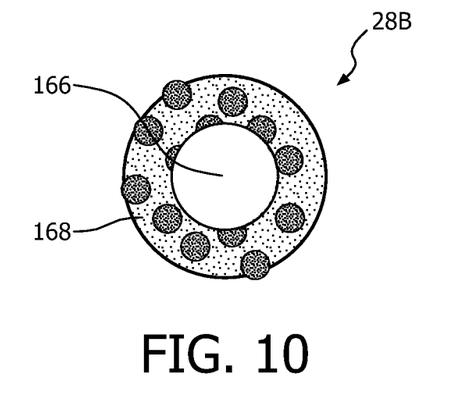
Figure 11:
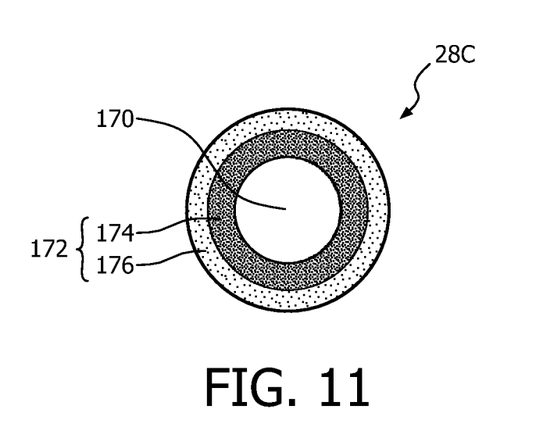

FIGS. 9-11 illustrate exemplary particles. As will be appreciated, these drawings are intended to be illustrative only and are not intended to be to scale. The particles can comprise a bleaching agent encapsulated in a shell.

In the particle 28A of FIG. 9, the particle includes a core 160 formed of a bleaching agent which is encapsulated by a shell 162 of a carrier material, such as shellac, which ruptures on impact with the teeth. The shell may be entirely formed of shellac or predominantly formed of shellac, e.g., at least 50 wt. %, or at least 80 wt. %, or at least 90 wt. % shellac.

Shellac is a natural, biodegradable and renewable resin of insect origin (Kerria lacca). It consists of a mixture of polyesters including polyhydroxy polycarboxylic esters, lactones and anhydrides and the main acid components are aleuritic acid and terpenic acid. Shellac has the features of low water permeability, and excellent film forming properties. It is enteric and listed as a food additive. Recently, methods to extract and purify shellac have significantly improved the stability of batch-to batch production and the use of an aqueous formulation of shellac (ammonium salt of shellac) has allowed elimination of the use of any organic solvents.

In one embodiment, particles 28A are formed according to the method described in Jing Xue and Zhibing Zhang, "Preparation and characterization of calcium-shellac spheres as a carrier of carbamide peroxide." In this method, an aqueous formulation of shellac (ammonium salt of shellac) is mixed with carbamide peroxide powder to dissolve the carbamide peroxide. Droplets of the resulting mixture are then dropped from a nozzle into a cross-linking solution comprising calcium chloride in ethanol to form solid particles of calcium shellac with hydrogen peroxide encapsulated. An ice bath can be used to maintain the temperature of the cross-linking solution at 4° C. A coaxial air stream with a flow rate, for example, of 90 liters/hr can be used to pull the liquid stream from the nozzle tip to create droplets and consistent particles. After the extrusion process, the particles formed in the cross-linking solution may be transferred into a stabilization solution of calcium chloride (at 4° C.) to increase the mechanical strength of the particles. The calcium shellac particles with carbamide peroxide encapsulated can be frozen by putting them into a freezer at 25° C. for 1 hr and then dried in a freeze dryer. A vacuum pump is switched on during the freeze drying process, which may be continued for 24 hr. The temperature in the drying chamber can be maintained at 25° C. with the aid of a fan.

In another method, particles 28A are formed as described in Jing Xue, Zhibing Zhang. "Physical, Structural, and Mechanical Characterization of Calcium—Shellac Microspheres as a Carrier of Carbamide Peroxide." In this method, an emulsification-gelation method is used in which calcium chloride powder is dispersed in an oil phase to encapsulate water-soluble carbamide peroxide. The carbamide peroxide is dissolved in shellac solution (ammonium salt of shellac). The mixture of carbamide peroxide and shellac is dispersed in an oil, such as sunflower oil by agitating the mixture, e.g., with a flat-blade disk turbine impeller at an agitation speed of 200 rpm for 30 min. $CaCl_2$ powder is added slowly into the dispersion. Agitation is maintained for another 2 hr. The formed microspheres settling at the bottom of the stirred vessel are then collected, washed with 2% Tween 80 solution, and dried at room temperature (about 24° C.) for 24 hr by freeze drying, as for the other method.

In other embodiments, the shell can comprise a hydrophobic material which adheres to the teeth, the particles further comprising a release rate modifier in contact with the hydrophobic material, which modifies the rate of release of bleaching agent from the particle. The hydrophobic material can comprise a waxy solid. The release rate modifier can be selected from the group consisting of polyethylene glycol, silica, water-soluble alkali metal salts, and combinations thereof. In the particle 28B of FIG. 10, for example, the particle includes a core 166 formed of a bleaching agent which is encapsulated in a shell 168, formed of the controlled release carrier material. The controlled release carrier material in shell 168 includes a hydrophobic material, serving as a matrix, such as a wax, and a release rate modifier in contact with, e.g., dispersed in, the hydrophobic material. The particle 28B adheres to the tooth and the integrity of the hydrophobic material is disrupted when the release rate modifier comes into contact with water. A ratio of the release rate modifier to hydrophobic material can be tailored to provide a slower or faster release rate of the hydrogen peroxide.

In the particle 28C of FIG. 11, the particle includes a core 170 formed of a bleaching agent which is encapsulated by a shell 172 of controlled release carrier material in the form of two layers 174, 176, the first, inner layer 174 comprising release rate modifier, and the second, outer layer 176 comprising hydrophobic material, such as a wax. The integrity of the hydrophobic material is disrupted when the particles collide with the teeth and the release rate modifier is thereby exposed and comes into contact with water. This enables a slow release of the hydrogen peroxide from the core over several hours. A ratio of the release rate modifier to hydrophobic material can be tailored to provide a slower or faster release rate of the hydrogen peroxide.

The hydrophobic material used to form the shell 168, 172 of particles 28B and 28C may be a waxy solid, i.e., is solid at ambient temperature (25° C.) and may be a solid at higher temperatures. The hydrophobic material may be primarily (greater than 50%) or entirely formed from a waxy solid. Exemplary waxes suitable to use as the hydrophobic material include hydrocarbon waxes, such as paraffin wax, and the like, which are substantially or entirely free of unsaturation. Exemplary paraffin waxes are mixtures of higher alkanes of the general formula $C_nH_{2n+2}$, where typically, $20 \leq n \leq 50$. They are solid at ambient temperatures and melt-processable.

The release rate modifier used for forming the shell 168, 172 of particles 28B and 28C may be a material which is insoluble or substantially insoluble in the hydrophobic material such that it forms discrete regions where it is of high concentration in the hydrophobic material (or a separate layer 174). The discrete regions have an average size of, for example, 0.1-100 nm, e.g., 0.5-20 nm.

The release rate modifier may be more hydrophilic than the hydrophobic material. Exemplary release rate modifiers include hydrophilic organic polymers which are capable of hydrogen bonding and that are solid at ambient temperatures (25° C.), and hydrophilic and/or water soluble powders. The release rate modifier may be present in the microparticles in a total concentration of from 0.001 wt. % to 30 wt. %. Examples of hydrophilic powders include anhydrous inorganic particles, such as silicon dioxide, e.g., hydrophilic silica and silica nanopowders. Exemplary water-soluble powders include water-soluble acids and salts thereof, such as anhydrous phosphate salts, e.g., sodium polyphosphate, sodium tripolyphosphate, sodium pyrophosphate; anhydrous citric acid and salts thereof, such as alkali metals salts, e.g., sodium citrate; anhydrous sodium sulfate, anhydrous magnesium salts, such as magnesium sulfate and magnesium chloride. Combinations of such release agents may be employed. The hydrophilic and/or water soluble powders, such as silica, may have an average size of, for example, 1-100 nanometers (nm), e.g., 5-20 nm. Hydrophilic fumed silica may be obtained under the tradename AEROSIL™ from Evonik Industries with a specific surface area (measured by the BET method) in the range of 90-300 m²/g. As an example, AEROSIL™ 200 has a specific surface area of 200 m²/g.

Hydrophilic organic polymers which are useful as release rate modifiers include polyalkylene glycols, such as polyethylene glycol and polypropylene glycol, and esters thereof, polyamide compounds (e.g., polyvinylpyrrolidone), poly(vinyl acetate), poly(vinyl alcohol), poly(acrylic acid), polyacrylamide, polyoxylglycerides, such as lauroyl, oleoyl, and stearoyl polyoxylglycerides, which are mixtures of monoesters, diesters, and triesters of glycerol and monoesters and diesters of polyethylene glycols (e.g., lauroyl macrogolglycerides), and ethylene oxide derivatives thereof, poloxamers, which are triblock copolymers having a central hydrophobic block of poly(propylene oxide) and two side blocks of poly(ethylene oxide) (e.g., poloxamer 188, which has a melting point 52° C.), and derivatives thereof, and mixtures thereof. The hydrophilic polymer can have a weight average molecular weight of at least 300.

Exemplary polyethylene glycols (PEG) for the release rate modifier have a molecular weight of 300 daltons to 50,000 daltons, e.g., 600-35000, or 1000 to 5,000 daltons. As examples PEG 1000 (melting point 37-40° C.), PEG 1500 (melting point 44-48° C.), PEG 2000 (melting point 49-52° C.), combinations thereof, and the like may be used.

A ratio of the hydrophobic material to release rate modifier in the particles may be, for example, from 1:99 to 99:1, expressed by weight, such as from 5:95 to 95:5 or from 10:90 to 90:10. For example, the ratio of hydrophobic material:release rate modifier may be about 30:70 to 70:30, for example, in the case of PEG. For hydrophilic and/or water soluble powders, the ratio may be higher, such as at least about 85:15.

The particles of types 28A, B, and C generally have a low water content, such as less than 5 wt. %, or less than 1 wt. %, or less than 0.2 wt. % of the particles is made up of water.

The particles of types 28A, B, and C may be used separately or combined in a container 34.

The microparticles 28 can be formed by a variety of methods including spray cooling, precipitation, and the like. Spray cooling/chilling methods can be used where the molten hydrophobic material containing the core material is sprayed into a cold chamber or onto a cooled surface and allowed to solidify. For example, small particles of carbamide peroxide, or other bleaching agent, are combined with a molten mixture of wax and release rate modifier, e.g., PEG. The mixture is sprayed through a nozzle into a fluid at a sufficiently low temperature to solidify the mixture as microparticles. For example, carbon dioxide at low temperature may be used as the cooling fluid. Other encapsulation techniques are disclosed in MICROENCAPSULATION: Methods and Industrial Applications, Edited by Benita and Simon (Marcel Dekker, Inc., 1996).

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A hand-held delivery device comprising:
  a source of pressurized fluid;
  a nozzle which defines an outlet;
  a fluid pathway which fluidly connects the source of pressurized fluid with the nozzle outlet for delivery of a spray of fluid from the nozzle outlet;
  a delivery mechanism which releases a dose of particles into the fluid pathway from an associated cartridge, such that the dose of the particles is carried by the pressurized fluid through the nozzle outlet in the spray, the particles comprising a dental care agent; and
  a housing which defines a channel, the housing comprising first and second sets of opposed openings to the channel;
  wherein the delivery mechanism includes a slider carried by the housing which receives the dose of particles from the cartridge, the slider being movable within the channel, relative to the cartridge, between first and second positions, wherein in the first position, the particles are received from the cartridge by the slider and the slider is positioned in the channel to block the fluid pathway at both sets of opposed openings to the channel and prevent the pressurized fluid from exiting the nozzle outlet, and wherein in the second position, both sets of opposed openings define a part of the fluid pathway connecting the source of pressurized fluid with the nozzle outlet, with the pressurized fluid flowing in one direction through the first sets of opposed openings and in an opposite direction in the second sets of openings, the particles are carried from the slider by the pressurized fluid.

2. The delivery device of claim 1, wherein the cartridge includes an opening, through which particles leave the cartridge, the hole opening being closed by the delivery mechanism against contact with the pressurized fluid.

3. The delivery device of claim 1, wherein in the first position, the slider closes first and second passageways through the delivery mechanism and in the second position, the passageways define a part of the fluid pathway.

4. The delivery device of claim 3, wherein the slider is slidably received in a channel defined by a housing.

5. The delivery device of claim 4, wherein the slider cooperates with the housing to define a cavity which is open at a first end to receive the dose of particles, and wherein in the first position, the housing closes a second end of the cavity, and in the second position, the housing defines an opening, allowing the pressurized fluid to enter the second end of cavity.

6. The delivery device of claim 1, further comprising:
a body portion which carries the source of pressurized fluid.

7. The delivery device of claim 1, wherein the source of pressurized fluid comprises a source of gas and a source of liquid which are combined in a mixing zone in the fluid pathway.

8. The delivery device of claim 1, wherein the delivery device comprises at least one actuation mechanism for controlling the device to supply the pressurized fluid and to actuate the delivery mechanism.

9. The delivery device of claim 8, wherein the actuation mechanism includes a pulsing mechanism for controlling the device to pulse bursts of the pressurized fluid and particles from the nozzle opening.

10. The delivery device of claim 1, wherein the dental care agent comprises a bleaching agent.

11. The delivery device of claim 10, wherein the bleaching agent is encapsulated in a shell.

12. The delivery device of claim 1, wherein the particles having a size of up to 100 μm in diameter.

13. The delivery device of claim 1, wherein the delivery device has a first mode of operation in which the fluid is delivered to the fluid pathway at a first fluid pressure and a second mode of operation in which the fluid is delivered to the fluid pathway at a second fluid pressure, lower than the first fluid pressure, one of the first and second modes being employed when the device is used to deliver the dose of particles and the other of the first and second modes being employed when the device is not used to deliver the particles.

14. A hand-held delivery mechanism comprising:
a housing which defines a channel;
a fluid pathway which fluidly connects a source of pressurized fluid with a nozzle outlet for delivery of a spray of fluid from the nozzle outlet; and
a slider carried by the housing, the slider being moveable, within the channel, between a first position, in which the slider accepts a dose of particles from an associated cartridge, and a second position, in which the dose of particles is released into the fluid pathway, the housing defining first and second sets of opposed openings to the channel which are closed by the slider when the slider is in the first position, and which are open to the channel when the slider is in the second position, wherein in the second position of the slider, the sets of opposed openings define a part of the fluid pathway connecting the source of pressurized fluid with the nozzle outlet and the dose of particles is positioned in the second set of opposed openings, with the pressurized fluid flowing in one direction through the first sets of opposed openings and in an opposite direction in the second sets of openings.

* * * * *